(12) United States Patent
Ru et al.

(10) Patent No.: US 12,414,217 B2
(45) Date of Patent: Sep. 9, 2025

(54) SYSTEMS AND METHODS FOR ADAPTIVELY CONTROLLING FILAMENT CURRENT IN AN X-RAY TUBE

(71) Applicant: Hologic, Inc., Marlborough, MA (US)

(72) Inventors: Guoyun Ru, Farmington, CT (US); David Aizer, Danbury, CT (US); J. Austin Fraley, Danbury, CT (US); Edward Nonnweiler, Brookfield, CT (US)

(73) Assignee: Hologic, Inc., Marlborough, MA (US)

( * ) Notice: Subject to any disclaimer, the term of this patent is extended or adjusted under 35 U.S.C. 154(b) by 219 days.

(21) Appl. No.: 18/100,683

(22) Filed: Jan. 24, 2023

(65) Prior Publication Data

US 2023/0251210 A1  Aug. 10, 2023

Related U.S. Application Data

(60) Provisional application No. 63/307,311, filed on Feb. 7, 2022.

(51) Int. Cl.
*H05G 1/26* (2006.01)
*A61B 6/58* (2024.01)
(Continued)

(52) U.S. Cl.
CPC ............ *H05G 1/34* (2013.01); *A61B 6/582* (2013.01); *H05G 1/265* (2013.01); *H05G 1/54* (2013.01); *A61B 6/502* (2013.01)

(58) Field of Classification Search
CPC . H05G 1/265; H05G 1/34; H05G 1/54; A61B 6/502; A61B 6/582
See application file for complete search history.

(56) References Cited

U.S. PATENT DOCUMENTS 3,365,575 A  1/1968 Strax
3,502,878 A  3/1970 Stewart
(Continued)

FOREIGN PATENT DOCUMENTS

CN  108492874  9/2018
DE   4104166  8/1992
(Continued)

OTHER PUBLICATIONS

"Essentials for life: Senographe Essential Full-Field Digital Mammography system", GE Health-care Brochure, MM-0132-05.06-EN-US, 2006, 12 pgs.
(Continued)

*Primary Examiner* — Thomas R Artman
(74) *Attorney, Agent, or Firm* — Merchant & Gould P.C.

(57) ABSTRACT

Systems and methods of adaptively controlling filament current in an x-ray tube of an imaging system include the x-ray tube having a filament being calibrated. Calibration data from the calibration of the x-ray tube is stored at the imaging system, the calibration data including a filament current value that determines a tube current value for a tube voltage value at a plurality of stations. A resistance value of the filament over a period of time is monitored. A change in the resistance value of the filament over the period of time is determined, and the filament current value of at least one of the plurality of stations is adjusted based on the changed resistance value.

19 Claims, 7 Drawing Sheets

(51) Int. Cl.
  *H05G 1/34* (2006.01)
  *H05G 1/54* (2006.01)
  *A61B 6/50* (2024.01)

(56) References Cited

U.S. PATENT DOCUMENTS

| | | | |
|---|---|---|---|
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,334,153 A | 6/1982 | Stehman |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,593,371 A | 6/1986 | Grajewski |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,799,248 A | 1/1989 | Furbee |
| 4,819,258 A | 4/1989 | Kleinman et al. |
| 4,821,727 A | 4/1989 | Levene et al. |
| 4,901,335 A | 2/1990 | Ferlic |
| 4,969,174 A | 11/1990 | Scheid et al. |
| 4,989,227 A | 1/1991 | Tirelli et al. |
| 4,998,270 A | 3/1991 | Scheid et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,077,773 A | 12/1991 | Sammon |
| 5,078,142 A | 1/1992 | Siczek et al. |
| 5,081,664 A | 1/1992 | Lie et al. |
| 5,129,911 A | 7/1992 | Siczek et al. |
| 5,142,557 A | 8/1992 | Toker |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,219,351 A | 6/1993 | Teubner |
| 5,240,011 A | 8/1993 | Assa |
| 5,256,370 A | 10/1993 | Slattery |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,451,789 A | 9/1995 | Wong |
| 5,452,367 A | 9/1995 | Bick et al. |
| 5,479,927 A | 1/1996 | Shmulewitz |
| 5,483,072 A | 1/1996 | Coe |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,606,589 A | 2/1997 | Pellegrino et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,242 A | 12/1998 | Jalink, Jr. |
| 5,844,965 A | 12/1998 | Galkin |
| 5,864,146 A | 1/1999 | Karellas |
| 5,872,828 A | 2/1999 | Niklason |
| 5,878,104 A | 3/1999 | Ploetz |
| 5,896,437 A | 4/1999 | Ploetz |
| 5,901,197 A | 5/1999 | Khutoryansky |
| 5,930,330 A | 7/1999 | Wolfe |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,081,577 A | 6/2000 | Webber |
| 6,091,841 A | 7/2000 | Rogers et al. |
| 6,101,236 A | 8/2000 | Wang et al. |
| 6,137,527 A | 10/2000 | Abdel-Malek et al. |
| 6,141,398 A | 10/2000 | He et al. |
| 6,149,301 A | 11/2000 | Kautzer et al. |
| 6,151,383 A | 11/2000 | Xue |
| 6,167,115 A | 12/2000 | Inoue |
| 6,175,117 B1 | 1/2001 | Komardin et al. |
| 6,196,715 B1 | 3/2001 | Nambu et al. |
| 6,207,958 B1 | 3/2001 | Giakos |
| 6,212,256 B1 | 4/2001 | Miesbauer |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,269,176 B1 | 7/2001 | Barski |
| 6,272,207 B1 | 8/2001 | Tang |
| 6,282,264 B1 | 8/2001 | Smith |
| 6,289,235 B1 | 9/2001 | Webber et al. |
| 6,292,530 B1 | 9/2001 | Yavus et al. |
| 6,292,531 B1 | 9/2001 | Hsieh et al. |
| 6,293,282 B1 | 9/2001 | Lemelson |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,351,517 B1 | 2/2002 | Guru |
| 6,375,352 B1 | 4/2002 | Hewes et al. |
| 6,399,951 B1 | 6/2002 | Paulus |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,453,009 B2 | 9/2002 | Berezowitz |
| 6,454,460 B1 | 9/2002 | Ramanathan |
| 6,459,925 B1 | 10/2002 | Nields et al. |
| 6,463,181 B2 | 10/2002 | Duarte |
| 6,480,565 B1 | 11/2002 | Ning |
| 6,490,476 B1 | 12/2002 | Townsend et al. |
| 6,496,557 B2 | 12/2002 | Wilson |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |

(56) References Cited

U.S. PATENT DOCUMENTS

| | | |
|---|---|---|
| 6,633,626 B2 | 10/2003 | Trotter |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,674,835 B2 | 1/2004 | Kaufhold |
| 6,702,459 B2 | 3/2004 | Barnes et al. |
| 6,744,848 B2 | 6/2004 | Stanton et al. |
| 6,748,044 B2 | 6/2004 | Sabol et al. |
| 6,748,046 B2 | 6/2004 | Thayer |
| 6,748,047 B2 | 6/2004 | Gonzalez |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,846,289 B2 | 1/2005 | Besson |
| 6,882,700 B2 | 4/2005 | Wang et al. |
| 6,885,724 B2 | 4/2005 | Li et al. |
| 6,895,076 B2 | 5/2005 | Halsmer |
| 6,901,132 B2 | 5/2005 | Eberhard |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,931,093 B2 | 8/2005 | Op De Beek et al. |
| 6,940,943 B2 | 9/2005 | Claus |
| 6,950,492 B2 | 9/2005 | Besson |
| 6,950,493 B2 | 9/2005 | Besson |
| 6,957,099 B1 | 10/2005 | Arnone et al. |
| 6,960,020 B2 | 11/2005 | Lai |
| 6,970,531 B2 | 11/2005 | Eberhard et al. |
| 6,970,586 B2 | 11/2005 | Baertsch |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,023,960 B2 * | 4/2006 | Chretien .................. H05G 1/34 378/112 |
| 7,092,482 B2 | 8/2006 | Besson |
| 7,104,690 B2 * | 9/2006 | Radley .................... H05G 1/54 378/207 |
| 7,110,490 B2 | 9/2006 | Eberhard |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 | 4/2007 | Betke |
| 7,218,766 B2 | 5/2007 | Eberhard |
| 7,244,063 B2 | 7/2007 | Eberhard |
| 7,245,694 B2 | 7/2007 | Jing et al. |
| 7,263,214 B2 | 8/2007 | Uppaluri |
| 7,286,645 B2 | 10/2007 | Freudenberger |
| 7,302,031 B2 | 11/2007 | Hjarn et al. |
| 7,315,607 B2 | 1/2008 | Ramsauer |
| 7,319,734 B2 | 1/2008 | Besson |
| 7,319,735 B2 | 1/2008 | Defreitas et al. |
| 7,319,736 B2 | 1/2008 | Rotondo |
| 7,323,692 B2 | 1/2008 | Rowlands et al. |
| 7,331,264 B2 | 2/2008 | Ozawa |
| 7,356,113 B2 | 4/2008 | Wu |
| 7,430,272 B2 | 9/2008 | Jing et al. |
| 7,433,507 B2 | 10/2008 | Jabri |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,609,808 B2 | 10/2009 | Tornai |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,241 B2 | 9/2010 | Wu |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,869,862 B2 | 1/2011 | Seppi |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,275,090 B2 * | 9/2012 | Ren ........................ A61B 6/025 378/21 |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,532,745 B2 | 9/2013 | DeFreitas et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 | 10/2014 | O'Connor |
| 8,873,716 B2 | 10/2014 | Ren et al. |
| 8,923,484 B2 * | 12/2014 | Zou ........................ H01J 35/28 378/126 |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,338,868 B2 * | 5/2016 | Yabugami ................ H05G 1/32 |
| 9,460,508 B2 | 10/2016 | Gkanatsios et al. |
| 9,498,175 B2 | 11/2016 | Stein et al. |
| 9,502,148 B2 | 11/2016 | Ren et al. |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,452,252 B2 | 10/2019 | Gkanatsios et al. |
| 10,614,996 B2 * | 4/2020 | Yonezawa ............. H01J 37/244 |
| 10,638,994 B2 | 5/2020 | DeFreitas |
| 10,719,223 B2 | 7/2020 | Gkanatsios |
| 10,753,969 B2 * | 8/2020 | Xu ........................ H05G 1/54 |
| 10,881,359 B2 | 1/2021 | Williams |
| 11,510,306 B2 | 11/2022 | Ru |
| 11,751,316 B2 * | 9/2023 | Duncan .................... H05G 1/54 378/104 |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 | 7/2002 | Dolazza |
| 2002/0113681 A1 | 8/2002 | Byram |
| 2002/0122533 A1 | 9/2002 | Marie et al. |
| 2002/0126798 A1 | 9/2002 | Harris |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |

(56) References Cited

U.S. PATENT DOCUMENTS

| | | |
|---|---|---|
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0149364 A1 | 8/2003 | Kapur |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049497 A1 | 3/2005 | Krishnan |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0084070 A1* | 4/2005 | Chretien ............... H05G 1/34 378/111 |
| 2005/0089205 A1 | 4/2005 | Kapur |
| 2005/0105679 A1 | 5/2005 | Wu et al. |
| 2005/0113681 A1 | 5/2005 | Defreitas |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0157849 A1 | 7/2005 | Radley |
| 2005/0226375 A1 | 10/2005 | Eberhard et al. |
| 2005/0248347 A1 | 11/2005 | Damadian |
| 2006/0009693 A1 | 1/2006 | Hanover et al. |
| 2006/0030784 A1 | 2/2006 | Miller et al. |
| 2006/0034426 A1 | 2/2006 | Freudenberger |
| 2006/0074288 A1 | 4/2006 | Kelly |
| 2006/0098855 A1 | 5/2006 | Gkanatsios et al. |
| 2006/0109951 A1 | 5/2006 | Popescu |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0257009 A1 | 11/2006 | Wang |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0189463 A1 | 8/2007 | Deuringer |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas |
| 2008/0118023 A1 | 5/2008 | Besson |
| 2008/0130979 A1 | 6/2008 | Ren |
| 2008/0198966 A1 | 8/2008 | Hjam |
| 2008/0212861 A1 | 9/2008 | Durgan et al. |
| 2008/0285712 A1 | 11/2008 | Kopans |
| 2008/0317196 A1 | 12/2008 | Imai |
| 2008/0317205 A1 | 12/2008 | Inuga et al. |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0135997 A1 | 5/2009 | Defreitas et al. |
| 2009/0141859 A1 | 6/2009 | Gkanatsios et al. |
| 2009/0143674 A1 | 6/2009 | Nields |
| 2009/0177495 A1 | 7/2009 | Abousy |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0268876 A1 | 10/2009 | Crucs |
| 2009/0281867 A1 | 11/2009 | Sievenpiper |
| 2009/0296882 A1 | 12/2009 | Gkanatsios |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0054401 A1 | 3/2010 | Blendl |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313019 A1 | 12/2010 | De Atley et al. |
| 2011/0026667 A1 | 2/2011 | Poorter |
| 2011/0069809 A1 | 3/2011 | Defreitas et al. |
| 2011/0087132 A1 | 4/2011 | DeFreitas et al. |
| 2011/0121969 A1 | 5/2011 | Mercer |
| 2011/0164724 A1 | 7/2011 | Ohta et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0237927 A1 | 9/2011 | Brooks et al. |
| 2011/0268246 A1 | 11/2011 | Dafni |
| 2012/0033868 A1 | 2/2012 | Ren |
| 2012/0039437 A1 | 2/2012 | Ren |
| 2012/0051502 A1 | 3/2012 | Ohta et al. |
| 2012/0236987 A1 | 9/2012 | Ruimi |
| 2012/0238870 A1 | 9/2012 | Smith et al. |
| 2013/0028374 A1 | 1/2013 | Gkanatsios et al. |
| 2013/0077748 A1 | 3/2013 | Althoff |
| 2013/0211261 A1 | 8/2013 | Wang |
| 2013/0223594 A1 | 8/2013 | Sprong |
| 2013/0272494 A1 | 10/2013 | DeFreitas et al. |
| 2013/0315378 A1* | 11/2013 | Yabugami ............... H05G 1/32 378/98 |
| 2014/0044230 A1 | 2/2014 | Stein et al. |
| 2014/0044231 A1 | 2/2014 | Defreitas et al. |
| 2014/0064456 A1 | 3/2014 | Zou |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0376690 A1 | 12/2014 | Jing et al. |
| 2015/0049859 A1 | 2/2015 | DeFreitas et al. |
| 2015/0117617 A1 | 4/2015 | Ishihara |
| 2015/0157880 A1 | 6/2015 | Dalbow |
| 2015/0160848 A1 | 6/2015 | Gkanatsios et al. |
| 2015/0310611 A1 | 10/2015 | Gkanatsios et al. |
| 2015/0347693 A1 | 12/2015 | Lam |
| 2015/0352376 A1 | 12/2015 | Wiggers |
| 2016/0106383 A1 | 4/2016 | Ren et al. |
| 2016/0120497 A1 | 5/2016 | Nasir |

(56) References Cited

U.S. PATENT DOCUMENTS

| | | |
|---|---|---|
| 2016/0188828 A1 | 6/2016 | Klingenberg |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0331339 A1 | 11/2016 | Guo |
| 2017/0024113 A1 | 1/2017 | Gkanatsios et al. |
| 2017/0128028 A1 | 5/2017 | DeFreitas et al. |
| 2017/0135650 A1 | 5/2017 | Stein et al. |
| 2017/0135653 A1 | 5/2017 | Ren |
| 2017/0215831 A1 | 8/2017 | Nagano |
| 2017/0319167 A1 | 11/2017 | Goto |
| 2017/0372863 A1 | 12/2017 | Price |
| 2018/0005796 A1 | 1/2018 | Iida |
| 2018/0068066 A1 | 3/2018 | Bronkalla |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0315579 A1 | 11/2018 | Yonezawa |
| 2018/0344276 A1 | 12/2018 | DeFreitas et al. |
| 2019/0059830 A1 | 2/2019 | Williams |
| 2019/0095087 A1 | 3/2019 | Gkanatsios et al. |
| 2019/0138693 A1 | 5/2019 | Meller |
| 2019/0159747 A1 | 5/2019 | Zanca |
| 2019/0188848 A1 | 6/2019 | Madani |
| 2019/0200942 A1 | 7/2019 | DeFreitas |
| 2019/0221304 A1 | 7/2019 | Ionasec |
| 2019/0295248 A1 | 9/2019 | Nakamura |
| 2019/0304736 A1 | 10/2019 | Matsuura |
| 2019/0317144 A1* | 10/2019 | Xu .................. H01J 35/025 |
| 2019/0320994 A1 | 10/2019 | Lemaitre |
| 2019/0336794 A1 | 11/2019 | Li |
| 2020/0012417 A1 | 1/2020 | Gkanatsios |
| 2020/0029927 A1 | 1/2020 | Wilson |
| 2020/0043600 A1 | 2/2020 | Glottmann |
| 2020/0085393 A1 | 3/2020 | Zhang |
| 2020/0167920 A1 | 5/2020 | Hall |
| 2020/0286613 A1 | 9/2020 | Rego |
| 2020/0348835 A1 | 11/2020 | Gkanatsios |
| 2020/0352531 A1 | 11/2020 | Smith |
| 2021/0136900 A1 | 5/2021 | Duncan |
| 2021/0176850 A1 | 6/2021 | Ru |
| 2021/0298700 A1 | 9/2021 | Williams |
| 2021/0303078 A1 | 9/2021 | Wells |
| 2021/0370098 A1 | 12/2021 | Flint |
| 2022/0037006 A1 | 2/2022 | Zan |
| 2023/0251210 A1* | 8/2023 | Ru .................. H05G 1/265 378/21 |
| 2024/0206044 A1* | 6/2024 | Pronk .................. H05G 1/54 |

FOREIGN PATENT DOCUMENTS

| | | |
|---|---|---|
| DE | 102004051401 | 5/2006 |
| DE | 102004051820 | 5/2006 |
| DE | 102010027871 | 10/2011 |
| DE | 102011007215 | 10/2012 |
| EP | 0775467 | 5/1997 |
| EP | 0982001 | 3/2000 |
| EP | 1028451 | 8/2000 |
| EP | 1428473 | 6/2004 |
| EP | 1623672 | 2/2006 |
| EP | 1759637 | 3/2007 |
| EP | 1569556 | 4/2012 |
| EP | 2732764 | 5/2014 |
| EP | 2602743 | 11/2014 |
| EP | 2819145 | 12/2014 |
| EP | 3143935 | 3/2017 |
| EP | 3569148 | 11/2019 |
| GB | 415709 | 8/1934 |
| JP | 53151381 U | 11/1978 |
| JP | H 05-329143 | 12/1993 |
| JP | H07-230778 | 8/1995 |
| JP | 2000-287960 | 10/2000 |
| JP | 2001-346786 | 12/2001 |
| JP | 2002219124 | 8/2002 |
| JP | 2004-511884 | 4/2004 |
| JP | 2004-188200 | 7/2004 |
| JP | 2004-528682 | 9/2004 |
| JP | 2005-142160 | 6/2005 |
| JP | 2006-519625 | 8/2006 |
| JP | 2006-231054 | 9/2006 |
| JP | 2007-50264 | 3/2007 |
| JP | 2007-054528 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2008-159317 | 7/2008 |
| JP | 2009500048 | 1/2009 |
| JP | 4-261864 | 4/2009 |
| JP | 2011-516116 | 5/2011 |
| JP | 2019-125460 A | 7/2019 |
| WO | 90/05485 | 5/1990 |
| WO | 9803115 | 1/1998 |
| WO | 98/16903 | 4/1998 |
| WO | 00/51484 | 9/2000 |
| WO | 2000068863 | 11/2000 |
| WO | 03/020114 | 3/2003 |
| WO | 03037046 | 5/2003 |
| WO | 2003/057564 | 7/2003 |
| WO | 2004/043535 | 5/2004 |
| WO | 2005/051197 | 6/2005 |
| WO | 2005/110230 | 11/2005 |
| WO | 2005/112767 | 12/2005 |
| WO | 2006/004185 | 1/2006 |
| WO | 2006055830 | 5/2006 |
| WO | 2006/058160 | 6/2006 |
| WO | 2007129244 | 11/2007 |
| WO | 2008072144 | 6/2008 |
| WO | 2009122328 | 10/2009 |
| WO | 2009136349 | 11/2009 |
| WO | 2010/070554 | 6/2010 |
| WO | 2013/184213 | 12/2013 |
| WO | 2019/030410 | 2/2019 |
| WO | 2016/057960 | 5/2019 |

OTHER PUBLICATIONS

"Filtered Back Projection," (NYGREN) published May 8, 2007; URL:http://web.archive.org/web/19991010131715/http://www.owlnet.rice.edu/-.about.e1ec539/Projects97/cult/node2.html., 2 pgs.

"Lorad Selenia" Document B-BI-SEO US/Intl (May 2006) copyright Hologic 2006, 12 pgs.

ACRIN website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.

American College of Radiology website, located at http://www.acr.org/FAQs/DBT-FAQ, "Digital Breast Tomosynthesis FAQ for Insurers", obtained online on Dec. 8, 2015, 2 pages.

Arfelli, F. et al., "Mammography with synchrotron radiation: phase-detection techniques", Apr. 2000, retrieved at: https://www.ncbi.nlm.nih.gov/pubmed/10751500, 8 pages.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.

Boone, J. et al., "Dedicated Breast CT: Radiation Dose and Image Quality Evaluation", Dec. 31, 2001, retrieved at: http://pubs.rsna.org/doi/abs/10.1148/radiol.2213010334,11 pages.

Chan, Heang-Ping et al., "ROC study of the effect of stereoscopic imaging on assessment of breast lesions", Medical Physics, vol. 32, No. 4, Apr. 2005, 7 pgs.

Choi, Bareum et al., "Surgical-tools detection based on Convolutional Neural Network in Laparoscopic Robot-Assisted Surgery", 2017 39th Annual Int'l. Conference of the IEEE Engineering in Medicine and Biology Society (EMBC), IEEE, Jul. 11, 2017, pp. 1756-1759.

Cole, Elodia, et al., "The Effects of Gray Scale Image Processing on Digital Mammography Interpretation Performance", Academic Radiology, vol. 12, No. 5, pp. 585-595, May 2005.

(56) References Cited

OTHER PUBLICATIONS

Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.
Grant, David G., "Tomosynthesis: a three-dimensional imaging technique", IEEE Trans. Biomed. Engineering, vol. BME-19, #1, Jan. 1972, pp. 20-28.
Hamberg, Leena M., "Tomosynthesis breast imaging: early detection and characterization of breast cancer", prepared by Massachusetts General Hospital for the U.S. Army Medical Research and Material Command Fort Detrick, Maryland, Jul. 2000, 20 pages.
Han et al., "MatchNet: Unifying Feature and Metric Learning for Patch-Based Matching", 2015 IEEE Conference on Computer Vision and Pattern Recognition (CVPR), Boston, MA, 2015, pp. 3279-3286.
Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.
Kapur, Ajay et al., "Combination of Digital Mammography with Semiautomated 3D Breast Ultrasound", Aug. 1, 2004, retrieved at: http://journals.sagepub.com/doi/abs/10.1177/153303460400300402, 10 pages.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kopans, D., "Development and Clinical Evaluation of Tomosynthesis for Digital Mammography", Oct. 31, 2000, retrieved at: http://oai.dtic.mil/oai/oai?verb=getRecord&metadataPrefix=html&identifier=ADA387722, 91 pages.
Kopans, Daniel B., "Breast Imaging", Chapter 26: Future Advances in Breast Imaging, 2nd Edition, Lippincott-Raven Publishers, Philadelphia, 1998, 37 pages.
Lehmann, V. et al., "MEMS techniques applied to the fabrication of anti-scatter grids for X-ray imaging", 2002, retrieved at: https://www.researchgate.net/profile/S_Ronnebeck/publication/222546207_MEMS_techniques_applied_to_the_fabrication_of_anti-scatter_grids_for_Xray_imaging/links/5570136f08aeccd777417301/MEMS-techniques-applied-to-the-fabrication-of-anti-scatter-grids-for-X-ray-imaging.pdf, 6 pages.
Mammographic Accreditation Phantom, http://www.cirsinc.com/pdfs/015cp.pdf. (2006), 2 pgs.
Niklason et al., "Digital breast tomosynthesis: potentially a new method for breast cancer screening", In Digital Mammography, 1998, 6 pages.
Niklason et al., "Digital Breast Imaging: Tomosynthesis and Digital Subtraction Mammography", Breast Disease, vol. 10, No. 3-4, pp. 151-164, 1998.
Niklason, Loren T. et al., "Digital Tomosynthesis in Breast Imaging", Radiology, Nov. 1997, vol. 205, No. 2, pp. 399-406.

Nykanen, Kirsi et al., "X-ray scattering in full-field digital mammography", Jul. 2003, retrieved at: http://www.siltanen-research.net/publ/NykanenSiltanen2003.pdf, 10 pages.
Pediconi, Federica et al., "Color-coded automated signal intensity-curve for detection and characterization of breast lesions: Preliminary evaluation of a new software for MR-based breast imaging", International Congress Series 1281 (2005) 1081-1086.
Pisano, Etta D., "Digital Mammography", Radiology, vol. 234, No. 2, Feb. 2005, pp. 353-362.
Rolf Behling—Ed-Behling et al., Chapter 6: Diagnostic X-Ray Sources from the Inside, Modern Diagnostic X-Ray Sources, Taylor & Francis Group, pp. 177-308, Jan. 1, 2016, retrieved from the internet on Jun. 26, 2015 at: https://ebookcentral.proquest.com/lib/epo-ebooks/detail.action?docID=2075866.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Smith, A., "Fundamentals of Breast Tomosynthesis", White Paper, Hologic Inc., WP-00007, Jun. 2008, 8 pgs.
Smith, Andrew, PhD, "Full Field Breast Tomosynthesis", Hologic White Paper, Oct. 2004, 6 pgs.
Suryanarayanan, S. et al., "Comparison of tomosynthesis methods used with digital mammography", Dec. 31, 2000, retrieved at: http://www.sciencedirect.com/science/article/pii/S1076633200800616, 13 pages.
Suryanarayanan, S. et al., "Evaluation of Linear and Nonlinear Tomosynthetic Reconstruction Methods in Digital Mammography", Mar. 2001, retrieved at: http://www.sciencedirect.com/science/article/pii/S1076633203805305, 6 pages.
Thurfjell, "Mammography screening: one versus two views and independent double reading", Acta Radiologica 35, No. 4, 1994, pp. 345-350.
Webber, Richard, "A controlled evaluation of tuned-aperture computed tomography applied to digital spot mammography", Feb. 2000, retrieved at: https://www.ncbi.nlm.nih.gov/pmc/articles/PMC3453191/, 8 pages.
Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wu, T. et al., "A comparison of reconstruction algorithms for breast tomosynthesis", Aug. 26, 2004, retrieved at: http://onlinelibrary.wiley.com/doi/10.1118/1.1786692/full.
Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.
European Extended Search Report in Application 23155076.5, mailed Jul. 7, 2023, 8 pages.
Zhao, Bo et al., "Imaging Performance of an Amorphous Selenium Digital Mammography Detector in a Breast Tomosynthesis System", Medical Physics, vol. 35, No. 5, Apr. 2008, pp. 1978-1987.

* cited by examiner

SYSTEMS AND METHODS FOR ADAPTIVELY CONTROLLING FILAMENT CURRENT IN AN X-RAY TUBE

CROSS-REFERENCE TO RELATED APPLICATIONS

This application claims priority to and the benefit of U.S. Provisional Application No. 63/307,311, filed Feb. 7, 2022, which is hereby incorporated by reference herein in its entirety.

BACKGROUND

Imaging based on the use of x-rays is commonplace in medical imaging technology, such as, but not limited to, mammography or tomosynthesis systems. The x-rays used in such imaging technology are often generated through the use of an x-ray tube. Inside the x-ray tube there is an anode and a cathode, and within the cathode there is a filament that emits electrons. The electrons are accelerated by an electrical field generated by applying a high voltage potential across the anode and cathode terminals. As the filament wears with use, the filament material evaporates under high temperature. This evaporation results in a thinning of the material and an increase in filament resistance. When the resistance of the filament increases, power and temperature at the filament are increased, thereby resulting in an increased radiation output.

SUMMARY

In one aspect, the technology relates to a method of adaptively controlling filament current in an x-ray tube of an imaging system, the method including: calibrating the x-ray tube having a filament; storing calibration data from the calibration of the x-ray tube at the imaging system, wherein the calibration data includes a filament current value that determines a tube current value for a tube voltage value at a plurality of stations; monitoring a resistance value of the filament over a period of time; determining a change in the resistance value of the filament over the period of time; and adjusting the filament current value of at least one of the plurality of stations based on the changed resistance value.

In an example, monitoring the resistance value of the filament over the period of time includes measuring the resistance value after a predetermined number of sequence exposures and storing each measured resistance value. In another example, measuring the resistance value after the predetermined number of sequence exposures includes applying a constant filament current value to the filament after each of the predetermined number of sequence exposures. In yet another example, the method further includes waiting a predetermined time period between an end of the predetermined number of sequence exposures and prior to applying the constant filament current value to the filament for resistance value measurement. In still another example, the filament current value of each of the plurality of station is updated based on the changed resistance value. In an example, determining the change in the resistance value includes comparing a difference between resistance values over the period of time to a predetermined benchmark.

In another example, the method further includes measuring a resulted tube current value from the x-ray tube at a sequence exposure having a stored tube current value and tube voltage value for a station of the plurality of stations; and comparing a difference between the measured resulted tube current value and the stored tube current value for the respective station. In yet another example, based on the difference between the measured resulted tube current value and the stored tube current value, the period of time is at least partially defined. In still another example, measuring resulted tube current value is performed pre-exposure or post-exposure of the sequence exposure. In an example, the method further includes determining a life-cycle period of the filament based at least partially on the monitored resistance value of the filament.

In another aspect, the technology relates to an imaging system includes: an x-ray tube having a filament; a current control circuit coupled to the x-ray tube and configured to channel current through the filament; at least one processor communicatively coupled to the current control circuit; and memory communicatively coupled to the at least one processor, the memory including computer executable instructions that, when executed by the at least one processor, performs a method including: calibrating the x-ray tube; storing calibration data from the calibration of the x-ray tube at the imaging system, wherein the calibration data includes a filament current value that determines a tube current value for a tube voltage value at a plurality of stations; monitoring a resistance value of the filament over a period of time; determining a change in the resistance value of the filament over the period of time; and adjusting the filament current value of at least one of the plurality of stations based on the changed resistance value.

In an example, monitoring the resistance value of the filament over the period of time includes measuring the resistance value after a predetermined number of sequence exposures and storing each measured resistance value. In another example, measuring the resistance value after the predetermined number of sequence exposures includes applying a constant filament current value to the filament after each of the predetermined number of sequence exposures. In yet another example, the method further includes waiting a predetermined time period between an end of the predetermined number of sequence exposures and prior to applying the constant filament current value to the filament for resistance value measurement. In still another example, the filament current value of each of the plurality of station is updated based on the changed resistance value. In an example, determining the change in the resistance value includes comparing a difference between resistance values over the period of time to a predetermined benchmark.

In another example, the method further includes: measuring a resulted tube current value from the x-ray tube at a sequence exposure having a stored tube current value and tube voltage value for a station of the plurality of stations; and comparing a difference between the measured resulted tube current value and the stored tube current value for the respective station. In yet another example, based on the difference between the measured resulted tube current value and the stored tube current value, the period of time is at least partially defined. In still another example, measuring resulted tube current value is performed pre-exposure or post-exposure of the sequence exposure. In an example, the method further includes determining a life-cycle period of the filament based at least partially on the monitored resistance value of the filament.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

DETAILED DESCRIPTION

As discussed above, x-ray tubes in medical imaging systems have limited lifetimes. The limited lifetime of x-ray tubes is often due to the high heat and high voltages that are generally required for the operation of the x-ray tube. The high heat and voltages cause the components of the x-ray tube to break down, and in some components, change performance characteristics. When the x-ray tube changes performance characteristics, the x-ray tube needs to be recalibrated, and in some instances replaced. Recalibration and/or replacement costs of the x-ray tube are often significant, and according, improvements to the x-ray tube are desired.

Based on analysis of x-ray tube filaments, as the filament degrades with use, the filament material evaporates and reduces its thickness. This results in the resistive properties of the filament changing and increasing. As the resistance of the filament increases, the power and the temperature generated at the filament increases during operation, causing an increase in radiation output from the x-ray tube.

The present technology relates to a feedback mechanism to adjust the filament current needed to maintain the required or desired x-ray radiation at each tube output current and tube voltage station as the filament resistance changes over time. For example, after calibration of the x-ray tube, the filament power (e.g., based on the filament current generated) for each tube output current and tube voltage station is calculated and saved by the control system. Over the operational life of the x-ray tube, the filament resistance is monitored. When the filament resistance changes by a predetermined amount, the filament current may be adjusted appropriately by the control system to get the filament power the same as the stored value for each tube output current and tube voltage station. As such, the x-ray tube can deliver the desired x-ray radiation even with the filament changing resistive characteristics. Additionally, recalibration procedures will be reduced as the x-ray tube degrades with use.

Figure 1:
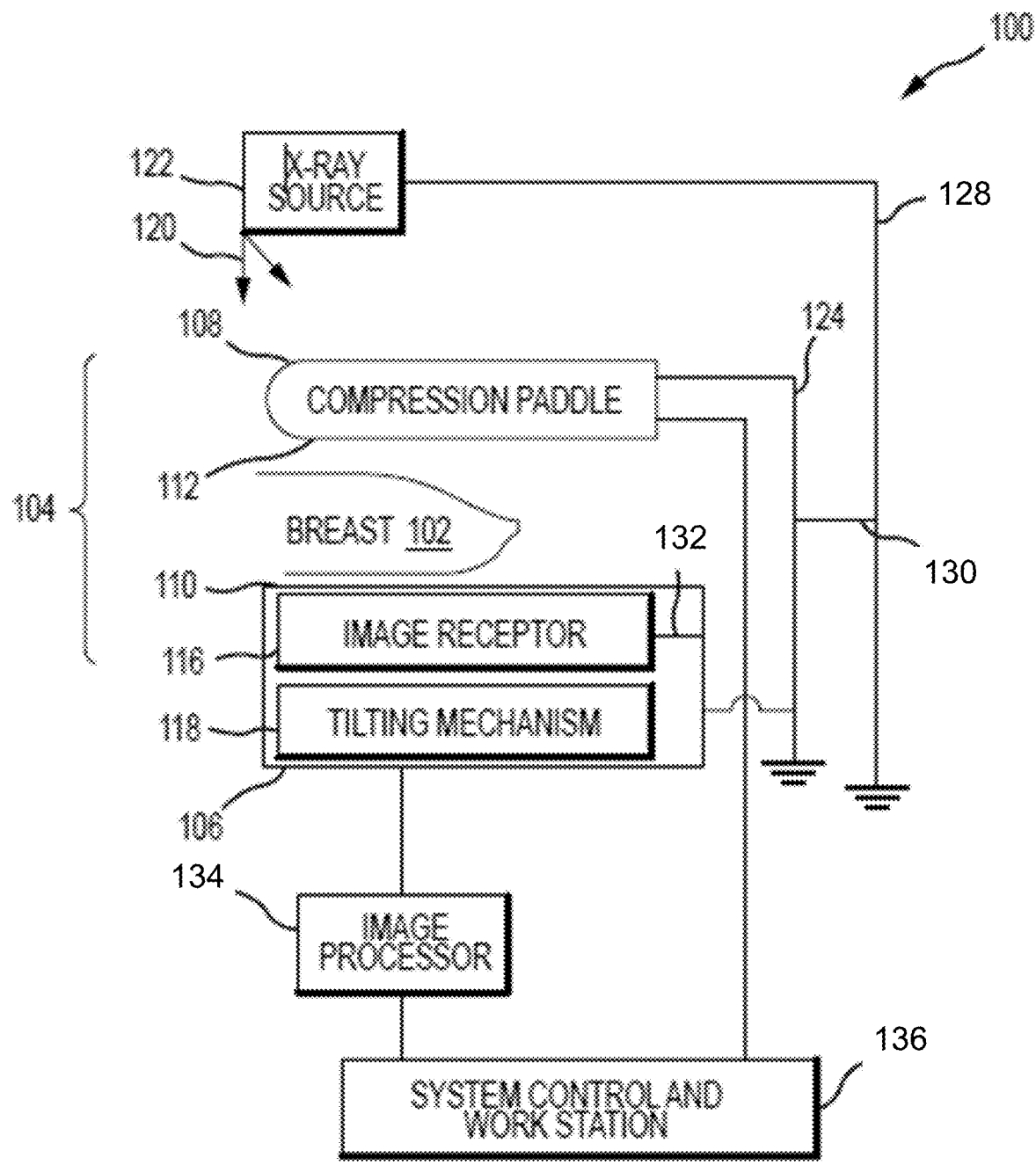
FIG. 1 is a schematic view of an exemplary imaging system.
Figure 2:
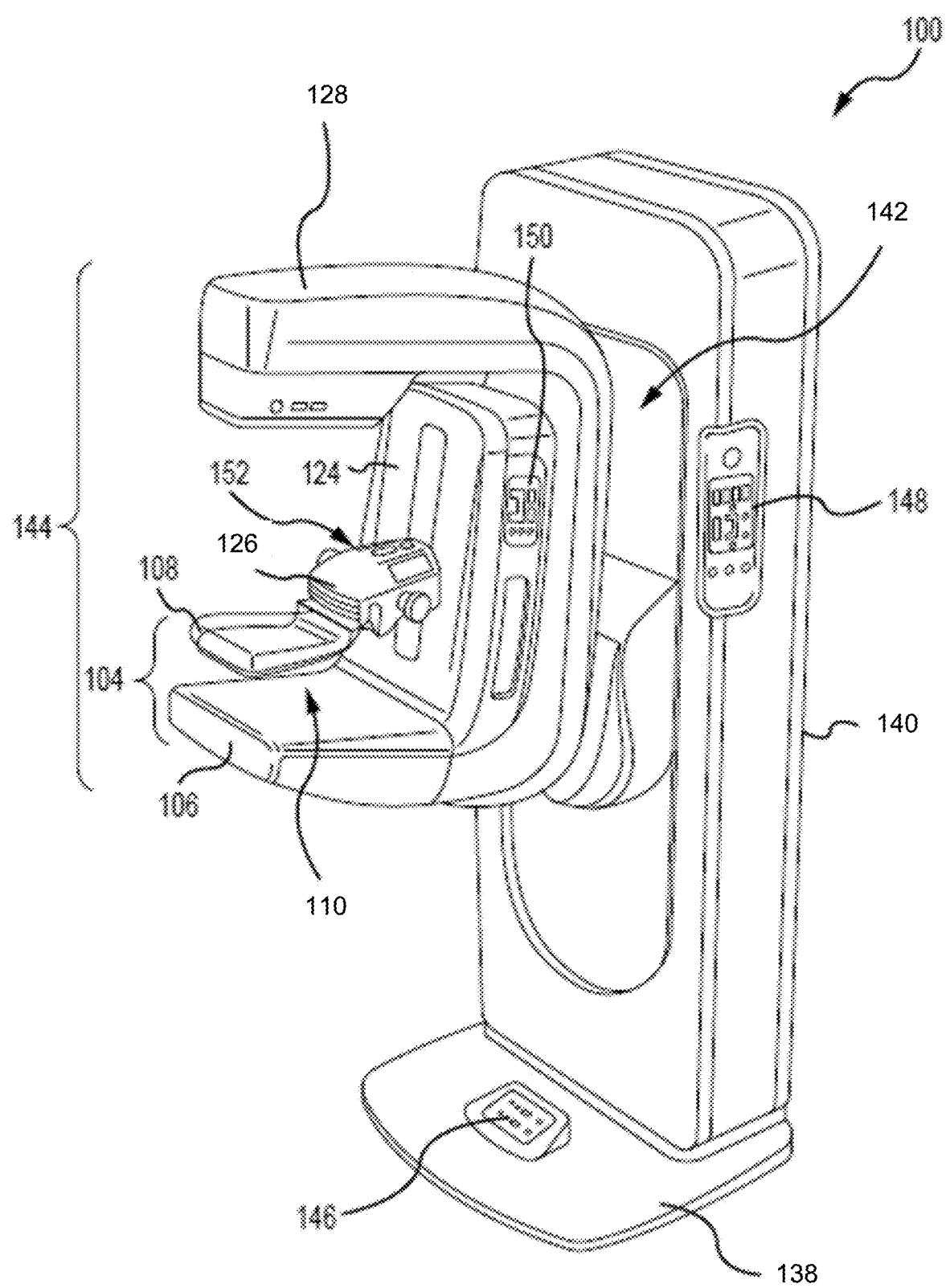
FIG. 2 is a perspective view of the imaging system of FIG. 1.

FIG. 1 is a schematic view of an exemplary imaging system 100. FIG. 2 is a perspective view of the imaging system 100. Referring concurrently to FIGS. 1 and 2, not every element described below is depicted in both figures. The imaging system 100 immobilizes a patient's breast 102 for x-ray imaging (either or both of mammography, tomosynthesis, or other imaging modalities) via a breast compression immobilizer unit 104 that includes a breast support platform 106 and a moveable compression paddle 108. The breast support platform 106 and the compression paddle 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 and the compression paddle 108 is supported on the first support arm 124 by a paddle mount 126, which is configured to be raised and lowered along the support arm 124. The x-ray source 122 is supported on a second support arm, also referred to as a tube head 128. For mammography, support arms 124 and 128 can rotate as a unit about an axis 130 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 128 to a different imaging orientation. For tomosynthesis, the support arm 124 stays in place, with the breast 102 immobilized and remaining in place, while at least the second support arm 128 rotates the x-ray source 122 relative to the immobilizer unit 104 and the compressed breast 102 about the axis 130. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 128. The tilting can be through the same angle as the rotation of the x-ray source 122, but may also be through a different angle selected such that the beam 120 remains substantially in the same position on the image receptor 116 for each of the plural images. The tilting can be about an axis 132, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, other modalities such as ultrasound, or a "combo" system that can perform multiple forms of imaging. An example of a system has been offered by the assignee hereof under the trade name Selenia Dimensions.

Whether operating in a mammography or a tomosynthesis mode, the system 100 images the breast 102 by emitting the x-ray beam 120 from the x-ray source 122. The x-ray beam 120 passes through the breast 102 where it is detected by the image receptor 116. The image receptor 116 may include a plurality of pixels that detect the intensity of the x-ray beam 120 at a plurality of locations after the x-ray beam 120 has passed through the breast 102. The attenuation of the x-ray beam 120 as it passes through the breast 102 changes depending on the structures of the breast 102. Accordingly, images of the breast 102 may be produced from the detected x-ray beam 120. For instance, the image receptor 116 produces imaging information in the form of electric signals, and supplies that imaging information to an image processor 134 for processing and generating x-ray images of the breast 102. A system control and work station unit 136 including software controls the operation of the system 100 and interacts with the operator to receive commands and deliver information including processed-ray images. The system control and work station unit 136 may also include software for controlling the operation of the x-ray source 122.

The imaging system 100 includes a floor mount or base 138 for supporting the imaging system 100 on a floor. A gantry 140 extends upwards from the floor mount 138 and rotatably supports both the tube head 128 and the support arm 124. The tube head 128 and support arm 124 are configured to rotate discretely from each other and may also be raised and lowered along a face 142 of the gantry 140 so as to accommodate patients of different heights. The x-ray source 122 is disposed within the tube head 128. Together, the tube head 128 and support arm 124 may be referred to as a C-arm 144. A number of interfaces and display screens are disposed on the imaging system 100. These include a foot display screen 146, a gantry interface 148, a support arm interface 150, and a compression arm interface 152. In general the various interfaces 146, 148, 150, and 152 may include one or more tactile buttons, knobs, switches, as well as one or more display screens, including capacitive touch screens with graphic user interfaces (GUIs) so as to enable user interaction with and control of the imaging system 100.

Figure 3:
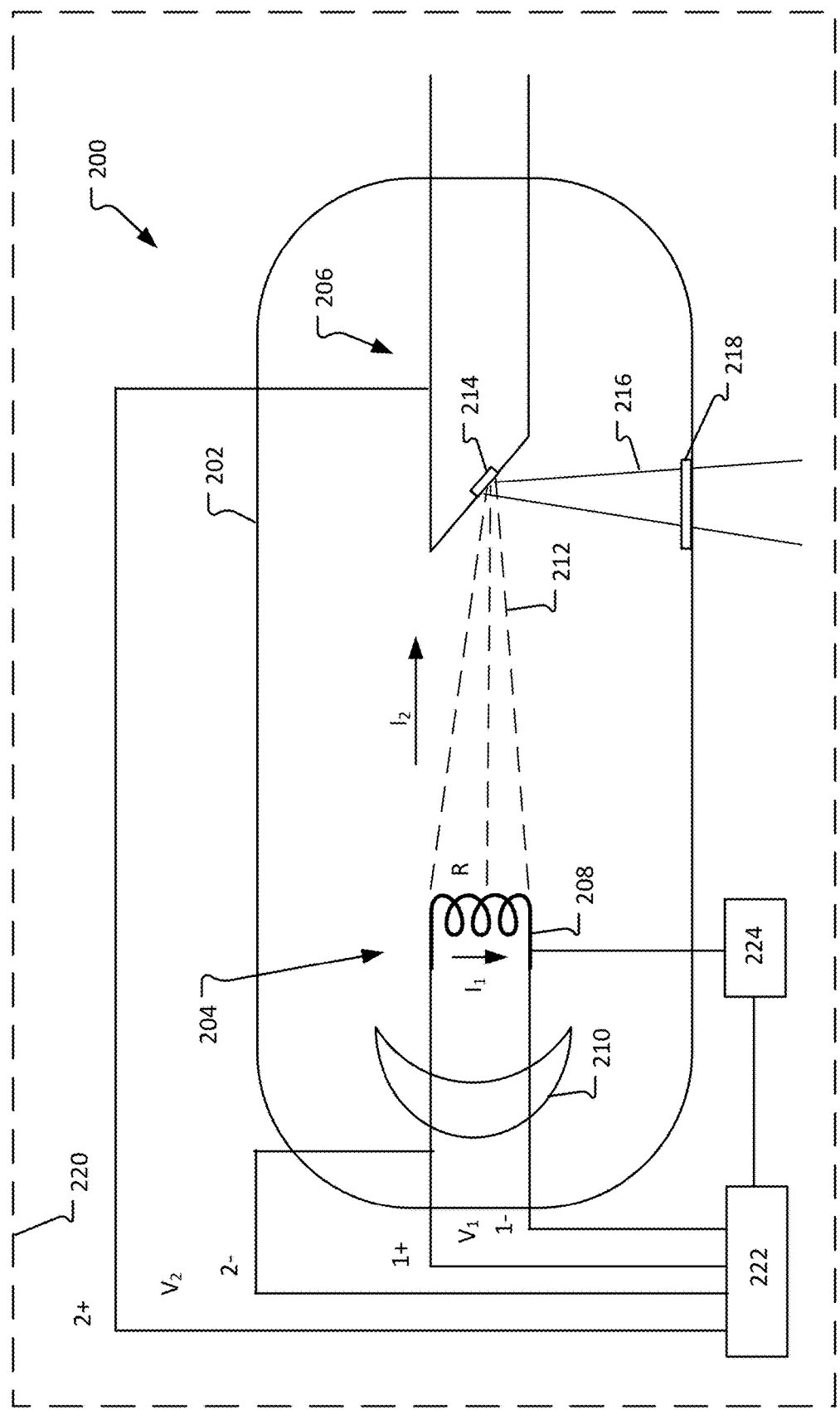
FIG. 3 is a schematic view of an x-ray tube.

FIG. 3 is a schematic view of an x-ray tube 200. The x-ray tube 200 may be included as at least part of the x-ray source 122 discussed above. The x-ray tube 200 includes a tube body 202 housing a cathode 204 and an anode 206. The cathode 204 includes a filament 208 and, in some examples, a focusing cup 210. The filament 208 can be placed adjacent the focusing cup 210 and between the focusing cup 210 and the anode 206. The filament 208 may be formed from a material with a high melting point, such as tungsten. A voltage or signal $V_1$ may be applied across the filament 208 via wires connected to each end of the filament 208, indicated by the 1+ for the positive connection to the filament 208 and the 1− for the negative connection to the filament 208. When the signal or voltage is applied across the filament 208, a current $I_1$ flows through the filament 208 which heats the filament 208 and causes electrons to be emitted from the filament 208. Due to a high voltage potential $V_2$ applied between the cathode 204 and the anode 206 as indicated by the 2+ for the positive connection to the anode 206 and the 2− for the negative connection to the cathode 204, the electrons emitted from the filament 208 are accelerated towards the anode 206. The accelerated electrons form an electron beam 212 that travels along an electron beam path between the cathode 204 and the anode 206. The electron beam 212 impacts the anode 206 at a focal spot 214 and causes the emission of x-rays 216 from the anode 206. The x-rays 216 exit the x-ray tube body 202 through a tube window 218. The x-rays 216 that exit from the body 202 form the x-ray beam that is used for imaging, such as the x-ray beam 120 discussed above with reference to FIGS. 1 and 2.

The area that the electron beam 212 impacts the anode 206 is referred to as the focal spot 214. This size of the focal spot 214 relates to the resolution required or desired for the imaging process. The location of the focal spot 214 on the anode 206, as well as, the angle of the anode 206, have an effect on the direction of the x-rays 216 produced from the anode 206. The size and location of the focal spot 214 may be controlled or modified by the focusing cup 210. Additionally, the electron beam 212 is produced by thermionic effect from the filament 208 being heated by the electric current $I_1$. This current value of the filament 208, via applied voltage $V_1$ across the filament 208, determines a tube output value $I_2$, typically measured in milliamperes (mA), for a given tube high voltage potential $V_2$, typically measured in kilovoltage (kV).

In the example, the x-ray tube 200 is included in a high voltage control circuit 220 (also known as a current control circuit) that is configured to control operation of the x-ray tube 200. The high voltage control circuit 220 may include a micro-computer 222 that stores operational data and processes for the x-ray tube 200 and facilitates operation of the x-ray tube 200. For example, the high voltage control circuit 220, via the micro-computer 222 coupled in communication with the x-ray tube 200, applies voltage $V_1$ across the filament 208 (e.g. via channeling current through the filament) based on stored calibration data so as to emit x-rays 216 having a required or desired radiation amount (e.g., radiation dose). In x-ray imaging, control of the amount of x-ray radiation for increased image quality is desired. In an aspect, the x-ray dose is proportional to the tube output value $I_2$ per second (mAs) for a given kV tube voltage potential $V_2$.

In operation, when a new x-ray tube 200 is installed in an x-ray imaging system, the current applied $I_1$ (e.g., via voltage $V_1$ generation) at the filament 208 is calibrated for a plurality of kV tube voltage $V_2$ and mA tube output $I_2$ stations. In an aspect, every x-ray tube 200 can have unique performance characteristics, and as such, each x-ray tube may have a slightly different calibration. Additionally, the x-ray tube 200 can also be re-calibrated as required or desired as performance characteristics change. As used herein, a station corresponds to discrete kV tube voltage $V_2$ and mA tube output $I_2$ values that produce, and reproduce, the same quantity of radiation during an exposure. In an aspect, power applied at the filament 208 is based at least partially on filament current $I_1$ and controls the tube output current values. However, as the filament 208 wears and degrades with use, the filament material evaporates under high temperature, which results in a thinning of the filament material and in turn, an increase of filament resistance R. As the resistance R increases in the filament 208, during operation of the x-ray tube, the power (e.g., via the voltage $V_1$ applied) generated at the filament 208 increases and the temperature of the filament 208 increases, thereby resulting in an increased radiation output from the same voltage $V_1$ being applied across the filament 208.

In some systems, the high voltage control circuit 220 may measure the mA tube output $I_2$ of the x-ray tube after every exposure sequence (e.g. via an ammeter or the like). As used herein, an exposure sequence is the x-ray emissions during a modality procedure. Accordingly, in some modalities, such as mammography, an exposure sequence may be a single emission and the mA tube output $I_2$ measurement occurs prior to firing the x-ray. In other modalities, such as tomo-synthesis, an exposure sequence may be a plurality of emissions and the mA tube output $I_2$ measurement occurs after firing the x-rays. This measured actual mA output value $I_2$ of the exposure sequence may then be compared to the desired mA output value $I_2$ for the exposure sequence. If the difference between the actual mA output value $I_2$ and the desired mA output value $I_2$ exceeds a predetermined threshold, then the control circuit 220 may prompt for a new filament calibration. In an aspect, the predetermined threshold may be based on how much different the actual output is from the desired output while still maintaining accurate and usable x-ray images. In some examples, the predetermined threshold may be between about 35%-20%. In other examples, the predetermined threshold may be about 33%. However, if the difference between the actual mA output value $I_2$ and the desired mA output value $I_2$ does not exceed the predetermined threshold, then the control circuit 220 can adjust the voltage $V_1$ being applied to the filament 208 for the next exposure sequence. This voltage adjustment by the control circuit 220 enables the subsequent measured mA output values $I_2$ to be closer to the desired mA output values $I_2$ and increase x-ray imaging performance.

Adjusting the voltage $V_1$ applied to the filament 208 in the process described above, however, only adjusts the voltage $V_1$ for the active kV tube voltage $V_2$ and mA tube output $I_2$ station relating to the specific the exposure sequence. The other stations (e.g., inactive stations) that are not in use do not gain the benefit of the voltage adjustment algorithm. Furthermore, the mA tube output $I_2$ measurements only account for the fact that the mA output has changed in the x-ray tube 200 and does not address the underlying tube characteristics that caused the changed mA output, and as such, the accuracy of the adjustments are reduced. Accordingly, and as described above, it is the resistive properties R of the filament 208 that change over time and result in the changing mA output values $I_2$ of the x-ray tube 200. Thus, and in the examples described herein, the high voltage control circuit 220 is configured to monitor the resistive properties R of the filament 208. As such, the current $I_1$ applied to the filament 208 (e.g., via voltage $V_1$) may be adjusted based on the monitoring of the resistance properties R of the filament 208. By using the resistive properties R of the filament 208, each and every kV tube voltage $V_2$ and mA tube output $I_2$ station can be adjusted, thereby increasing x-ray imaging performance. Additionally, the accuracy of the adjustments from the x-ray tube calibration baseline values are increased because the adjustments are based on the underlying changing characteristics of the filament 208 that cause the change in mA output values $I_2$.

In the example, the high voltage control circuit 220 can include a monitoring instrument 224 operatively controlled by the micro-computer 222 to monitor the resistance values R of the filament 208. In an aspect, the monitoring instrument 224 may be a multimeter or the like that is configured to measure electrical properties of the filament 208, such as one or more of voltage, resistance, and current. Additionally or alternatively, the monitoring instrument 224 can calculate resistance R of the filament 208 using Ohm's law when the current and voltage applied across the filament 208 are known. The control circuit 220 also may be configured with a clock or other time keeping instrument whereby elapsed time may be monitored and certain operations can be performed at predetermined time sampling periods, intervals, or cycles. Accordingly, when the resistance R of the filament 208 changes by a certain amount over time, an algorithm for the control circuit 220 can adjust the filament current $I_1$, via the voltage $V_1$, to get the filament power the same as the stored calibration value for each kV tube voltage $V_2$ and mA tube output $I_2$ station. This leads to the x-ray tube 200 being capable of delivering the required or desired mA tube output value $I_2$ even with changing filament resistance values R.

Figure 4:
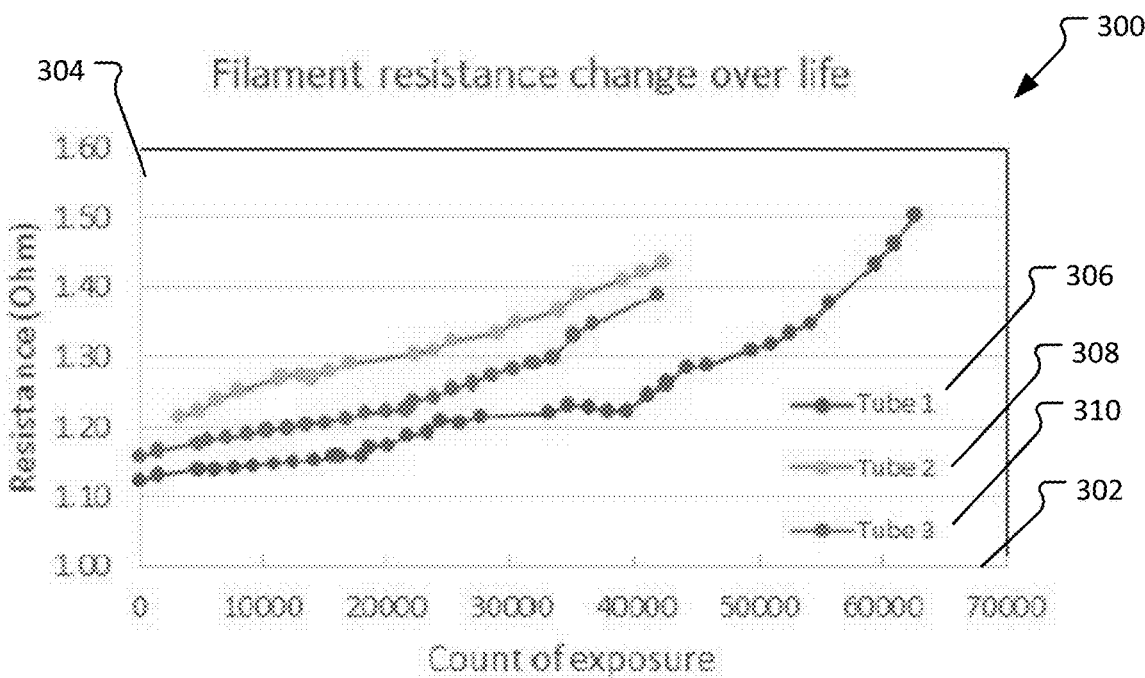
FIG. 4 is a graph depicting filament resistance change over a life of an x-ray tube.

FIG. 4 is a graph 300 depicting filament resistance change over a life of the x-ray tube 200 (shown in FIG. 3). As described above, the change in the resistance properties of the filament 208 (shown in FIG. 3) changes over the operational life of the x-ray tube 200 due to evaporation of filament material under high temperatures. The graph 300 has an x-axis 302 that counts the number of exposures of the x-ray tube 200, and thus, is a time component for the filament 208. In the example, the x-ray exposures are at a 33 kV tube voltage and a 200 mA tube current with 60 mAs. The mAs is the product of tube current in mA and time in seconds. A y-axis 304 charts the resistance in Ohms of the filament 208. As illustrated in the graph 300, three different x-ray tubes 306, 308, 310 are shown to have their filament resistance change during the operational use of the x-ray tubes. Each x-ray tube 306, 308, 310 is slightly different because all x-ray tubes are unique due to the design and manufacture of the individual x-ray tubes. However, all of the x-ray tubes 306, 308, 310 demonstrate that filament resistance values generally increase over time. This time period of change is over a period ten-thousand plus exposure counts, and thus, filament resistance does not change noticeably after every exposure count.

As used herein, the term "life" or "life-cycle" of the x-ray tube does not necessarily mean the life cycle to a point of physical failure. Rather, "life" or "life cycle" refers to a period of usage after which the x-ray tube no longer performs as required or desired.

Figure 5:
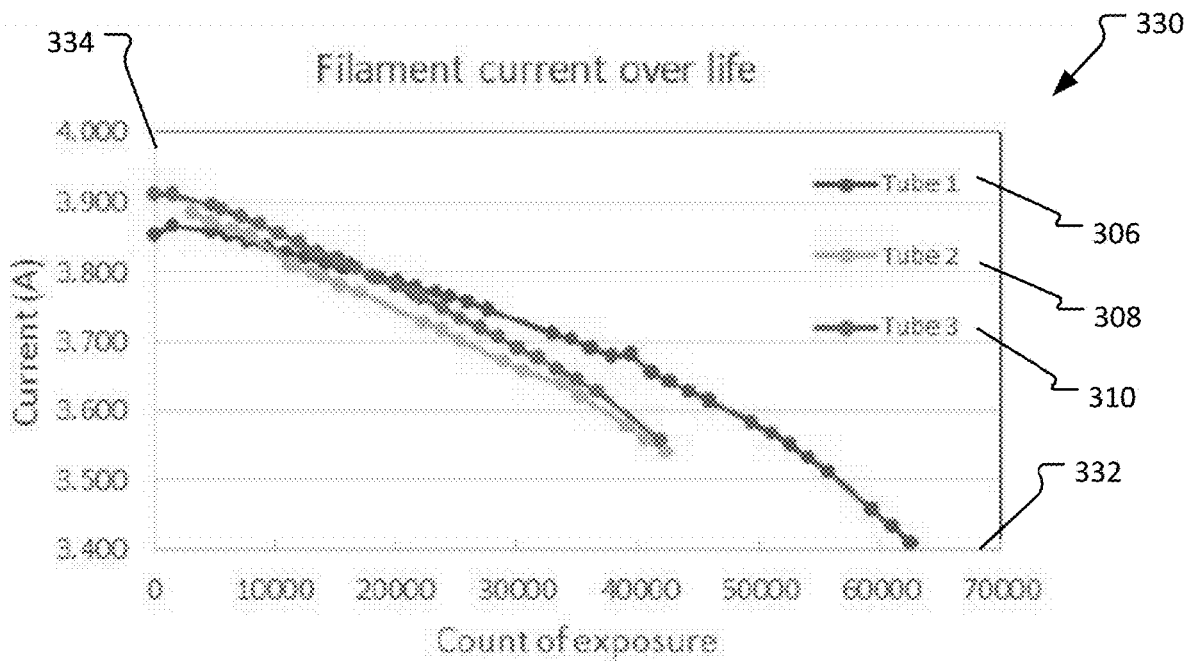
FIG. 5 is a graph depicting filament current change over the life of an x-ray tube.

FIG. 5 is a graph 330 depicting filament current change over the life of the x-ray tube 200 (shown in FIG. 3). As discussed in reference to FIG. 4 above, the resistance properties of the filament 208 (shown in FIG. 3) changes during operational use of the x-ray tube 200. Accordingly, as the filament resistance changes, the current applied at the filament 208 has to be changed during the operational use of the x-ray tube 200 to get desired tube output. The graph 330 has an x-axis 332 that counts the number of exposures of the x-ray tube 200, and thus, is a time component for the filament 208. A y-axis 334 charts the current in amperes of the filament 208. The graph 330 shows the filament current of the same three x-ray tubes 306, 308, 310 as FIG. 4 and at 33 kV tube voltage and 200 mA tube output. The curves illustrate the change in the filament current needed to maintain a constant 200 mA tube output as the filament resistance value increases over time.

Typically, when a new x-ray tube is installed in an imaging system, the filament current is calibrated for the required or desired kV tube voltage and mA tube current stations and these calibration values are stored within the system so that imaging can occur with the correct amount of x-ray radiation. This calibration process also occurs during recalibration of the x-ray tube 200. However, as shown in the graphs 300, 330, the resistive properties of the filament 208 changes and the filament current being applied at the filament 208 has to be reduced in order to deliver the required or desired mA tube output value. This is because as the filament resistance rises, the power at the filament 208 increases (e.g., power $P=I_2 \times R$) and the temperature of the filament increases if filament current is not adjusted, resulting in increased radiation output at the x-ray tube 200. As described herein, monitoring the change in resistance values of the filament 208 and generating feedback control of the x-ray tube 200 based on the filament resistance allows the filament current to be adjusted to maintain a required or desired x-ray radiation at each kV tube voltage and mA tube output station.

Figure 6:
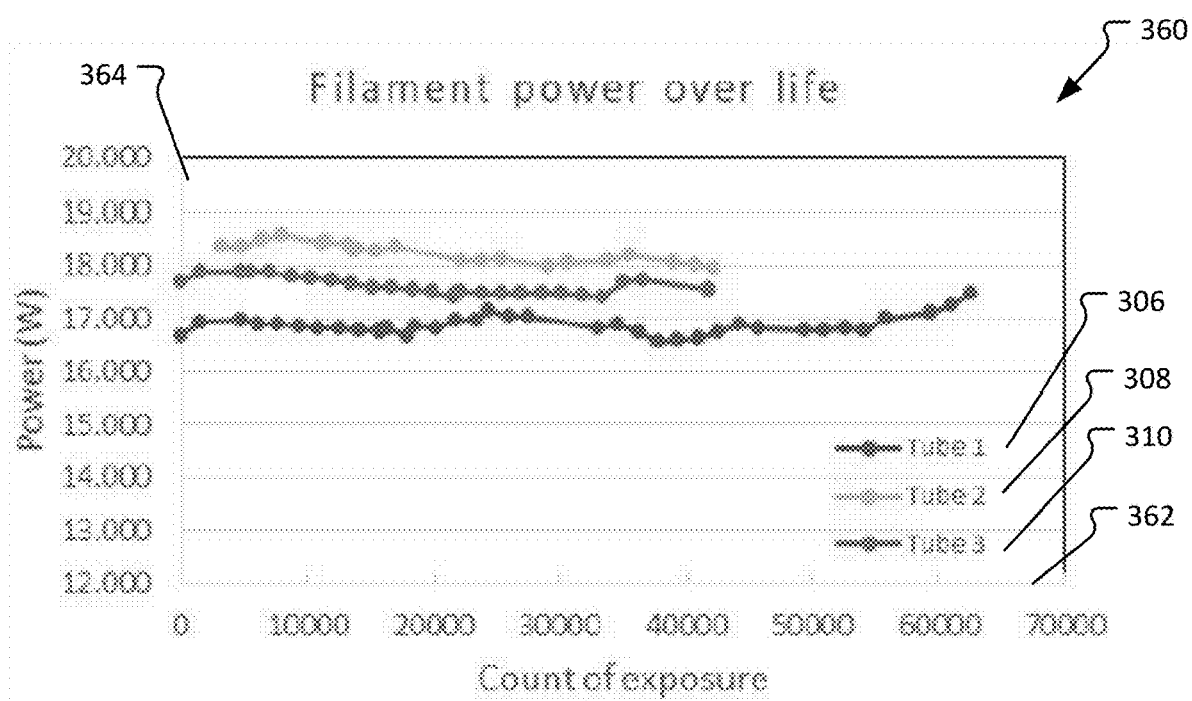
FIG. 6 is a graph depicting filament power change over the life of an x-ray tube.

FIG. 6 is a graph 360 depicting filament power change over the life of the x-ray tube 200 (shown in FIG. 3). The graph 360 has an x-axis 362 that counts the number of exposures of the x-ray tube 200, and thus, is a time component for the filament 208 (shown in FIG. 3). A y-axis 364 charts the power in watts of the filament 208. The graph 360 shows the filament power of the same three x-ray tubes 306, 308, 310 as FIGS. 4 and 5, and at a 33 kV tube voltage and 200 mA tube output. These curves demonstrate that to maintain the same mA tube output over the life of the x-ray tube 200 it is required to maintain the same filament power as right after filament current calibration for each kV tube voltage and mA tube output station. As such, to keep mA tube output within a required or desired value with filament resistance increasing over time, the filament current must be adjusted periodically to operate at a proper filament current for each station.

Referring to FIGS. 4-6, the graphs illustrate that filament current adjustment over life of the filament is needed to get a required or desired tube current mA. While FIGS. 4-6 are illustrative of a single station, the algorithm described herein can adjust filament current across active and inactive stations within the imaging system.

Figure 7:
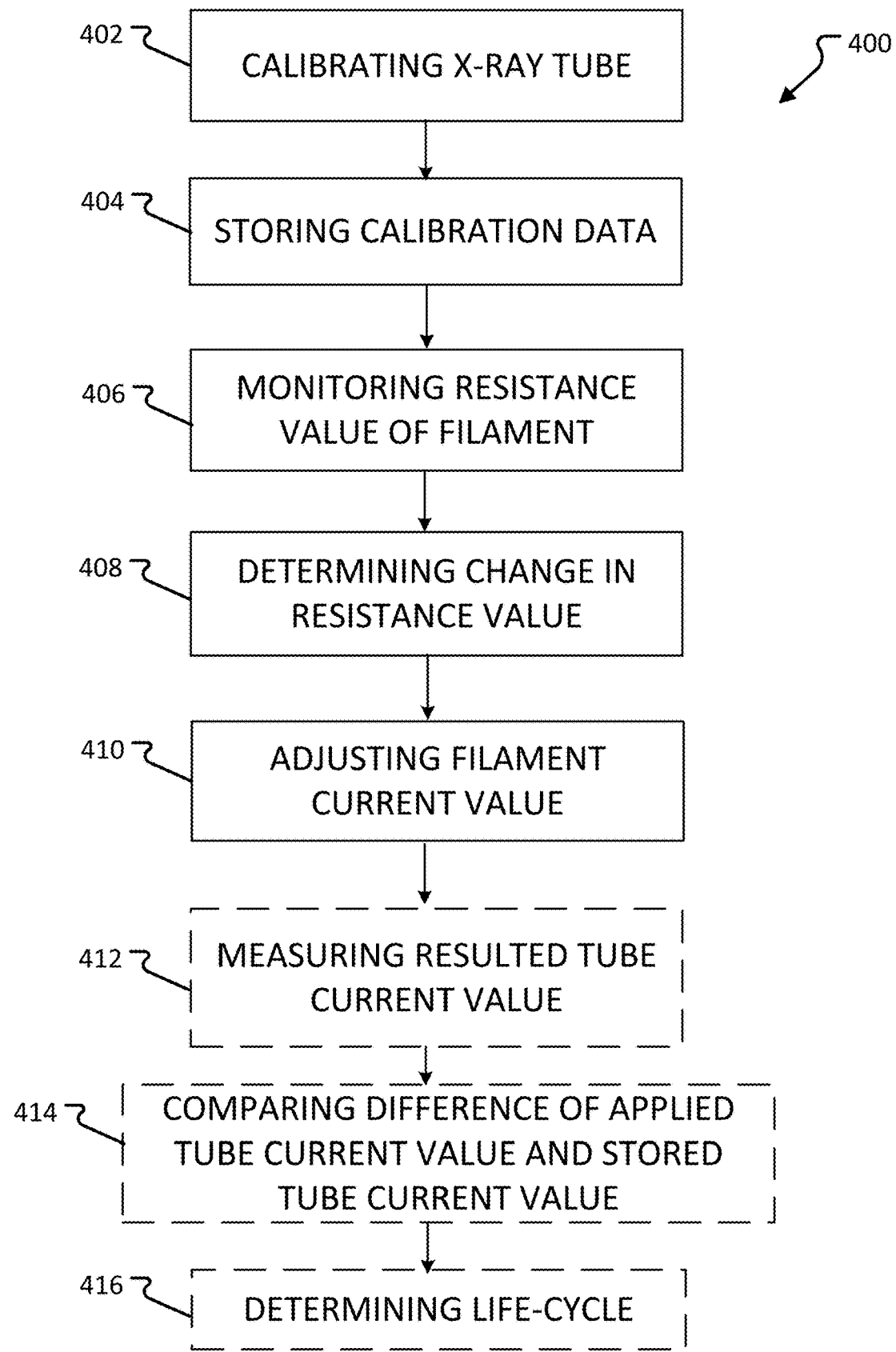
FIG. 7 depicts a flowchart illustrating a method of adaptively controlling filament current in an x-ray tube.

FIG. 7 depicts a flowchart illustrating a method 400 of adaptively controlling filament current in an x-ray tube. The example methods and operations can be implemented or performed by the systems and devices described herein (e.g., the imaging system 100 and x-ray tube 200 shown in FIGS. 1-3). The method 400 begins with calibrating (or re-calibrating) the x-ray tube having a filament therein (operation 402) and storing the calibration data at the imaging system (operation 404). In an aspect, the calibration data includes a filament current value that determines a tube output value for a tube voltage value at a plurality of stations that is generated from the calibration of the x-ray tube. Each station is defined by the tube output value in mA and the tube voltage value in kV so that a required or desired x-ray radiation amount is generated by the x-ray tube. In some examples, the filament current value may include a filament voltage value that is applied across the filament to generate the current value. The x-ray calibration procedure can be performed by methods that are currently known (e.g., a substitution method) or developed in the future. Because every x-ray tube has slightly different performance characteristics, calibration enables accurate operation of the imaging system as described herein.

The method 400 continues with monitoring a resistance value of the filament over a period of time (operation 406). As described above, the filament material evaporates under high temperatures and results in a thinning of the filament material, thereby increasing filament resistance over the operational lifetime of the x-ray tube. In an aspect, monitoring the resistance value of the filament may include measuring the resistance value after a predetermined number of sequence exposures and storing each measured resistance value. Based on the stored resistance values a resistance curve can be generated. In an example, the period of time for monitoring the resistance value can be based on the number of exposure counts and for example resistance values can be measured every 100 sequence exposures since it is known that resistance changes in an order many times this predetermined number. In other examples, the resistance value can be measured after every sequence exposure and stored as required or desired. As such, measuring and storing the resistance value is performed periodically.

In the example, measuring the resistance value includes applying a constant and known filament current value to the filament so as to measure the resistance. In an aspect, filament voltage is applied so that the filament receives about 2.5 amps to measure the resistance since voltage, current, and resistance are related via Ohm's law. Because each sequence exposure generates heat at the filament, in some examples, prior to measuring the resistance value, the filament is allowed to cool so as to increase accuracy of the resistance value measurement. In an example, cooling the filament can include waiting a predetermined time period between an end of the sequence exposures and prior to applying the constant filament current value for measuring the resistance value of the filament.

Turning back to the method 400, once the resistance value of the filament is being monitored (operation 406), a change in the resistance value of the filament is determined over the period of time (operation 408). Because the resistive characteristics of the filament change slowly after every exposure, and the tolerance for each exposure does allow for some change to the tube current output, the filament current value does not need to be revised or adjusted for every exposure count. As such, the change in resistance value can be determined by comparing a difference between resistance values over a period of time to a predetermined benchmark. For example, the predetermined benchmark may be a 4% resistance value change over at least 10,000 exposure counts. It should be appreciated that other predetermined benchmark values are also contemplated herein. For example, but not limiting, the resistance value change may be 2%, 5%, 10%, or the like, and the exposure count may be 5,000, 8,000, 12,000, or the like as required or desired.

Once it has been determined that the resistance value of the filament has changed (operation 408), then the filament current value is adjusted for at least one of the plurality of stations based on the changed resistance value (operation 410). By adjusting the filament current applied at the filament, the power at the filament during operation can be the same as the calibrated data for the tube current value and the tube voltage value for the station. Accordingly, the x-ray tube can deliver the required or desired tube current value even with an ever changing filament resistance value. In an aspect, the filament current value of each of the plurality of stations is updated based on the changed resistance value. As such, the calibration data can be adjusted based on the current resistive properties of the filament, and less active stations are still configured for a more accurate tube current value output the next time those stations are used for imaging procedures. In an aspect, adjusting the filament current value is based on a power model, whereby the filament power is maintained as right after initial filament calibration.

In the example, once the filament current value is adjusted the process may repeat itself with monitoring the resistance value over a new and reset period of time, determining change in the resistance value, and further adjust the filament current value as required or desired. This feedback algorithm for the resistance value enables the imaging system to operate longer between maintenance operations that calibrate/re-calibrate the x-ray tube.

In aspects, the method 400 may further include measuring a resulted tube current value from the x-ray tube at a sequence exposure having a stored tube current value and tube voltage value for a station of the plurality of stations (operation 412), and comparing a difference between the measured resulted tube current value and the stored tube current value for the respective station (operation 414). By measuring the resulted mA tube output current from the x-ray tube during operation and comparing the measured value to the stored desired output, operational data of the x-ray tube may be generated. For example, the accuracy of the feedback algorithm can be verified by this operational data, and if the adjusted filament current value results in less accurate tube current output values, a new filament calibration may be required. In another example, if the difference between the measured tube output current and the desired output is higher than a predetermined threshold, a new filament calibration may be required.

In other examples, based on the difference between the measured resulted tube current value and the stored tube current value, the period of time is at least partially defined. For example, instead of monitoring the resistance value based on the number of exposure counts, the resistance value can be monitored based on the operational results of the tube head, and if the difference between the measured tube current and the stored desired tube current exceeds a predetermined threshold, the change in resistance value can be used to adjust the filament current value as described above. In aspects, the measurement of the resulted tube current value may be performed pre-exposure or post-exposure of the sequence exposure. For example, in tomosynthesis imaging modalities the tube current measurements may be performed post-exposure, while in mammography imaging modalities the tube current measurement may be performed pre-exposure.

The method 400 may also include using the monitored resistance value of the filament to determine a life-cycle period of the filament (operation 416). For example, because filament resistance increases during the operational life of the filament due to filament material evaporating, an upper limit of filament resistance can be defined that relates to the filament material being too thin and triggering a tube replacement and a new filament calibration for the new x-ray tube.

Figure 8:
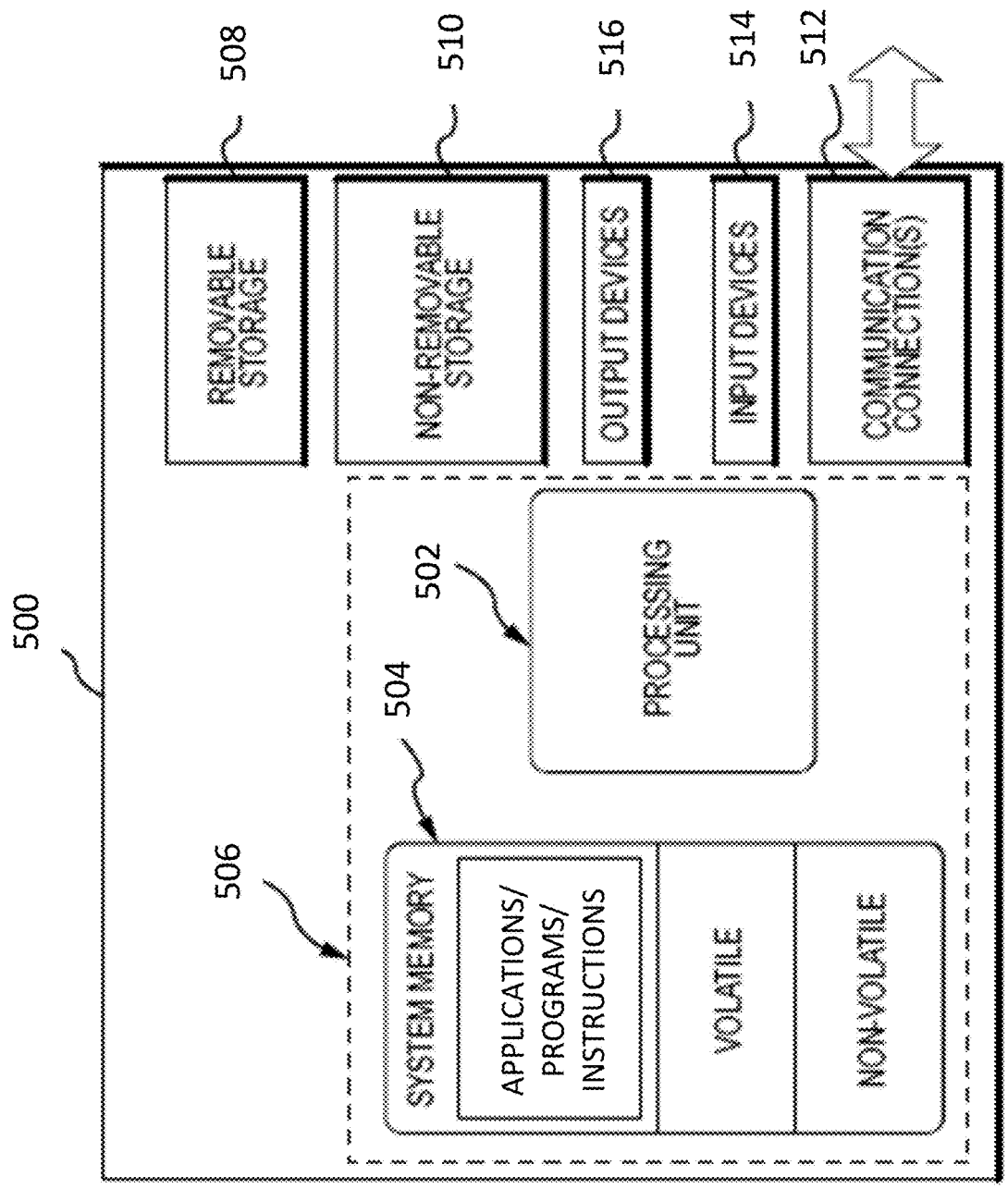
FIG. 8 depicts an example of a suitable operating environment for use with the present examples.

FIG. 8 illustrates an exemplary suitable operating environment 500 for controlling an x-ray tube. This operating environment may be incorporated directly into the high voltage control circuit disclosed herein, or may be incorporated into a computer system discrete from, but used to control the breast imaging systems described herein. Such computer system may be, for example, the system control and work station 136 depicted in FIG. 1. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 500 typically includes at least one processing unit 502 and memory 504. Depending on the exact configuration and type of computing device, memory 504 (storing, among other things, instructions to read from data storage devices or sensors, or perform other methods disclosed herein) can be volatile (such as RAM), non-volatile (such as ROM, flash memory, etc.), or some combination of the two. This most basic configuration is illustrated in FIG. 8 by dashed line 506. Further, environment 500 can also include storage devices (removable, 508, and/or non-removable, 510) including, but not limited to, magnetic or optical disks or tape. Similarly, environment 500 can also have input device(s) 514 such as touch screens, keyboard, mouse, pen, voice input, etc., and/or output device(s) 516 such as a display, speakers, printer, etc. Also included in the environment can be one or more communication connections 512, such as LAN, WAN, point to point, Bluetooth, RF, etc. In embodiments, the connections may be operable to facility point-to-point communications, connection-oriented communications, connectionless communications, etc.

Operating environment 500 typically includes at least some form of computer readable media. Computer readable media can be any available media that can be accessed by processing unit 502 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 500 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

This disclosure describes some examples of the present technology with reference to the accompanying drawings, in which only some of the possible examples were shown. Other aspects may, however, be embodied in many different forms and should not be construed as limited to the examples set forth herein. Rather, these examples were provided so that this disclosure was thorough and complete and fully conveyed the scope of the possible examples to those skilled in the art. Further, as used herein and in the claims, the phrase "at least one of element A, element B, or element C" is intended to convey any of: element A, element B, element C, elements A and B, elements A and C, elements B and C, and elements A, B, and C. Additionally, one having skill in the art will understand the degree to which terms such as "about" or "substantially" convey in light of the measurement techniques utilized herein. To the extend such terms may not be clearly defined or understood by one having skill in the art, the term "about" shall mean plus or minus ten percent.

Although specific examples were described herein, the scope of the technology is not limited to those specific examples. One skilled in the art will recognize other examples or improvements that are within the scope and spirit of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of adaptively controlling filament current in an x-ray tube of an imaging system, the method comprising:
    calibrating the x-ray tube having a filament;
    storing calibration data from the calibration of the x-ray tube at the imaging system, wherein the calibration data includes a filament current value that determines a tube current value for a tube voltage value at a plurality of exposure values;
    monitoring a resistance value of the filament over a period of time, wherein monitoring the resistance value includes measuring the resistance value of the filament after a predetermined number of sequence exposures and storing each measured resistance value;
    determining a change in the resistance value of the filament over the period of time, wherein the determined changed resistance value is based on a difference between the stored measured resistance values over a number of exposure counts; and
    adjusting the filament current value of at least one of the plurality of exposure values based on the determined changed resistance value.

2. The method of claim 1, wherein measuring the resistance value after the predetermined number of sequence exposures includes applying a constant filament current value to the filament after each of the predetermined number of sequence exposures.

3. The method of claim 2, further comprising waiting a predetermined time period between an end of the predetermined number of sequence exposures and prior to applying the constant filament current value to the filament for resistance value measurement.

4. The method of claim 1, wherein the filament current value of each of the plurality of exposure values is updated based on the changed resistance value.

5. The method of claim 1, wherein determining the change in the resistance value includes comparing a difference between resistance values over the period of time to a predetermined benchmark.

6. The method of claim 1, further comprising:
    measuring a resulted tube current value from the x-ray tube at a sequence exposure having a stored tube current value and tube voltage value for an exposure value of the plurality of exposure values; and
    comparing a difference between the measured resulted tube current value and the stored tube current value for the respective exposure value.

7. The method of claim 6, wherein based on the difference between the measured resulted tube current value and the stored tube current value, the period of time is at least partially defined.

8. The method of claim 6, wherein measuring resulted tube current value is performed pre-exposure or post-exposure of the sequence exposure.

9. The method of claim 1, further comprising determining a life-cycle period of the filament based at least partially on the monitored resistance value of the filament.

10. An imaging system comprising:
    an x-ray tube having a filament;
    a current control circuit coupled to the x-ray tube and configured to channel current through the filament;
    at least one processor communicatively coupled to the current control circuit; and
    memory communicatively coupled to the at least one processor, the memory comprising computer executable instructions that, when executed by the at least one processor, performs a method comprising:
    calibrating the x-ray tube;
    storing calibration data from the calibration of the x-ray tube at the imaging system, wherein the calibration data includes a filament current value that determines a tube current value for a tube voltage value at a plurality of exposure values;
    monitoring a resistance value of the filament over a period of time, wherein monitoring the resistance value includes measuring the resistance value of the filament after a predetermined number of sequence exposures and storing each measured resistance value;
    determining a change in the resistance value of the filament over the period of time, wherein the determined changed resistance value is based on a difference between the stored measured resistance values over a number of exposure counts; and
    adjusting the filament current value of at least one of the plurality of stations exposure values based on the determined changed resistance value.

11. The imaging system of claim 10, wherein measuring the resistance value after the predetermined number of sequence exposures includes applying a constant filament current value to the filament after each of the predetermined number of sequence exposures.

12. The imaging system of claim 11, wherein the method further comprises waiting a predetermined time period between an end of the predetermined number of sequence exposures and prior to applying the constant filament current value to the filament for resistance value measurement.

13. The imaging system of claim 11, wherein the filament current value of each of the plurality of exposure values is updated based on the changed resistance value.

14. The imaging system of claim 10, wherein determining the change in the resistance value includes comparing a difference between resistance values over the period of time to a predetermined benchmark.

15. The imaging system of claim 10, wherein the method further comprises:
measuring a resulted tube current value from the x-ray tube at a sequence exposure having a stored tube current value and tube voltage value for an exposure value of the plurality of exposure values; and
comparing a difference between the measured resulted tube current value and the stored tube current value for the respective exposure value.

16. The imaging system of claim 15, wherein based on the difference between the measured resulted tube current value and the stored tube current value, the period of time is at least partially defined.

17. The imaging system of claim 15, wherein measuring resulted tube current value is performed pre-exposure or post-exposure of the sequence exposure.

18. The imaging system of claim 10, wherein the method further comprises determining a life-cycle period of the filament based at least partially on the monitored resistance value of the filament.

19. A method of adaptively controlling filament current in an x-ray tube of an imaging system, the method comprising:
calibrating the x-ray tube having a filament;
storing calibration data from the calibration of the x-ray tube at the imaging system, wherein the calibration data includes a filament current value that determines a tube current value for a tube voltage value at a plurality of exposure values;
monitoring a resistance value of the filament over a period of time;
determining a change in the resistance value of the filament over the period of time;
adjusting the filament current value of at least one of the plurality of exposure values based on the changed resistance value;
measuring a resulted tube current value from the x-ray tube at a sequence exposure having a stored tube current value and tube voltage value for an exposure value of the plurality of exposure values; and
comparing a difference between the measured resulted tube current value and the stored tube current value for the respective exposure value, wherein based on the difference between the measured resulted tube current value and the stored tube current value, the period of time is at least partially defined.

* * * * *